(12) United States Patent
Bruder et al.

(10) Patent No.: US 9,060,733 B2
(45) Date of Patent: Jun. 23, 2015

(54) METHOD, COMPUTER SYSTEM AND CT SYSTEM FOR DETERMINING A MOTION FIELD AND FOR MOTION-COMPENSATED RECONSTRUCTION USING SAID MOTION FIELD

(71) Applicant: Siemens Aktiengesellschaft, Munich (DE)

(72) Inventors: Herbert Bruder, Höchstadt (DE); Christopher Rohkohl, Bochum (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 325 days.

(21) Appl. No.: 13/626,184

(22) Filed: Sep. 25, 2012

(65) Prior Publication Data

US 2013/0077843 A1    Mar. 28, 2013

(30) Foreign Application Priority Data

Sep. 28, 2011   (DE) .......................... 10 2011 083 643

(51) Int. Cl.
*G06K 9/00* (2006.01)
*A61B 6/00* (2006.01)
*A61B 6/03* (2006.01)

(52) U.S. Cl.
CPC ............... *A61B 6/4441* (2013.01); *A61B 6/032* (2013.01); *A61B 6/503* (2013.01); *A61B 6/5205* (2013.01); *A61B 6/5264* (2013.01); *A61B 6/507* (2013.01)

(58) Field of Classification Search
None
See application file for complete search history.

(56) References Cited

U.S. PATENT DOCUMENTS

| 2006/0002504 A1* | 1/2006 | De Man et al. ................ 378/4 |
| 2010/0195888 A1 | 8/2010 | Bruder |
| 2012/0189102 A1* | 7/2012 | Maurer et al. ................ 378/65 |
| 2012/0281896 A1* | 11/2012 | Aspelmeier et al. .......... 382/131 |

FOREIGN PATENT DOCUMENTS

DE    102009007236 A1    8/2010

OTHER PUBLICATIONS

Rohkohl, Christopher. Motion estimation and compensation for interventional cardiovascular image reconstruction. Diss. Erlangen, Nürnberg, Univ., Diss., 2010, 2011.*
Schäfer et al.; Motion-Compensated and Gated Cone Beam Filtered Back-Projection for 3-D Rotational X-Ray Angiography IEEE Trans Med Imaging. Jul. 2006; vol. 25, No. 7, pp. 898-906; Magazine; 2006.
H.Schöndube et al., "Evaluation of a novel CT image reconstruction algorithm with enhanced temporal resolution", Proc. SPIE 7961, Medical Imaging 2011: Physics of Medical Imaging, 79611N (Mar. 16, 2011).
C. Rohkohl Motion Estimation and Compensation for Interventional Cardiovascular Image Reconstruction pp. 1-128 Erlangen, 2011; Others; 2011; DE.
German Office Action for German Application No. DE 10 2011 083 643.8 dated May 16, 2012.

\* cited by examiner

*Primary Examiner* — Nirav G Patel
(74) *Attorney, Agent, or Firm* — Harness, Dickey & Pierce, P.L.C.

(57) ABSTRACT

A method is disclosed for determining a motion field in an image space of a CT image data set for a partially and cyclically moving object, wherein a projection data set from a CT system covering a motion phase and a projection angle range is recorded, and an iterative determination of the motion field by minimizing a cost function from CT image data sets which are motion-compensated and reconstructed making use of motion fields and which have a first image resolution, with a first analytical reconstruction algorithm, the cost function being based on raw data or transformed into the image space. A method for generating a motion-compensated CT image data set for a partially and cyclically moving object is also disclosed, along with a computer system for image reconstruction and a CT system.

23 Claims, 4 Drawing Sheets

METHOD, COMPUTER SYSTEM AND CT SYSTEM FOR DETERMINING A MOTION FIELD AND FOR MOTION-COMPENSATED RECONSTRUCTION USING SAID MOTION FIELD

PRIORITY STATEMENT

The present application hereby claims priority under 35 U.S.C. §119 to German patent application number DE 10 2011 083 643.8 filed Sep. 28, 2011, the entire contents of which are hereby incorporated herein by reference.

FIELD

At least one embodiment of the invention generally relates to a method for determining a motion field comprising a large number of location-specific motion vectors in a CT image data set for a partially and cyclically moving object. At least one embodiment of the invention also generally relates to a method for generating a motion-compensated CT image data set for a partially and cyclically moving object. Furthermore, at least one embodiment of the invention concerns a computer system for image reconstruction and a CT system with a computer system of this type, wherein the aforementioned methods are carried out during operation.

BACKGROUND

It is generally known that heart movements during CT imaging cause the recorded data to be inconsistent and also lead to image artifacts which severely restrict the clinical usefulness of the data. In order to prevent such image artifacts, in modern CT cardiac imaging, phase-related representation of the heart is generated by the recording and use of cardiac phase-related data. In this context, there are fundamentally a retrospective acquisition scheme and a prospective acquisition scheme. In the prospective acquisition scheme, only data gathered in a specific window around the rest phase of the heart are recorded and used for image reconstruction. The common aim of these approaches is effectively to freeze the motion of the heart, in order to minimize data inconsistency and thereby to maximize the image quality.

However, with a gantry rotation which is too slow relative to the heart motion or with a heartbeat which is too fast relative to the gantry motion, such strategies are not sufficient to achieve a high enough temporal resolution for calculating an artifact-free image. A variety of algorithms for improving the temporal resolution retrospectively is known in the prior art.

The publication by H. Schöndube, T. Allmendinger, K. Stierstorfer, H. Bruder, and T. Flohr entitled "Evaluation of a novel CT image reconstruction algorithm with enhanced temporal resolution" in: Proceedings of SPIE, p. 79611 N, 2011, describes a reduction in the data quantity required by undershooting the theoretical angular sampling of 180°, wherein due to the incomplete data, the image quality has to be optimized iteratively.

Furthermore, the publication by D. Schafer, J. Borgert, V. Rasche, and M. Grass entitled "Motion-Compensated and Gated Cone Beam Filtered Back-Projection for 3-D Rotational X-Ray Angiography", in IEEE Transactions on Medical Imaging, Vol. 25, No. 7, pp. 898-906, July 2006, discloses that with known object motion of the data used for reconstruction, said motion can be taken into account during a motion-compensated reconstruction. This procedure leads to a significant improvement in image quality.

Finally, reference is made to the document DE 10 2009 007 236 A1 in which a motion-compensated CT-reconstruction method for an at least partially moving object is disclosed. In this method, the moving object under investigation is scanned with a CT system and sectional images of the object under investigation are computed, with the recorded detector data using an iterative algorithm, wherein the iterative algorithm takes account of motion information concerning the motion of the object under investigation during data recording. This motion information is represented in the form of a motion field comprising a large number of location-specific vectors which describe the motion or the displacement of the object at the respective location at the time point of the recording. For determination of the motion field, it is proposed that two chronologically separated CT images are compared in order, from the change in the CT images, to deduce the location-specific motion.

So far unsolved in this regard, however, is the problem of correctly estimating the motion in order to improve the image quality of the "best-phase" image, that is, the image from a phase of optimum rest and therefore of the highest quality. Previous approaches merely estimate the movement by registering two 3-D standard reconstructions of different heart phases. However, so far, no improvement in the quality of the "best phase" image has been achieved, since such improvement inherently restricts the temporal resolution of the registered data. On the other hand, the images of poorer cardiac phases have been significantly improved with the result, for example, that the imaging of a different cardiac phase with improved image quality is made possible.

SUMMARY

At least one embodiment of the invention to provide a method and a CT system or a computer system for image reconstruction which reduces the remaining image artifacts by improved determination of the motion of the heart or by improved determination of a motion field for subsequent correction of the image data.

Advantageous developments of the invention are the subject matter of the subclaims.

At least one embodiment of the invention is directed to a method for determining a motion field, comprising a large number of location-specific motion vectors in an image space of a CT image data set for a partially and cyclically moving object, in particular from a patient with a beating heart, comprising the following method steps:

detection or transfer of a projection data set from a computed tomography system covering a pre-determined motion phase and a projection angle range, which enables the direct reconstruction of a CT image data set, iterative determination of the motion field by minimizing a cost function from CT image data sets which are motion-compensated and reconstructed making use of motion fields and which have a first image resolution, with a first analytical reconstruction algorithm, said cost function being transformed into the image space, and storage and/or output of the motion field.

On the basis of least one embodiment of the method described above for determining the motion field, a method for generating a motion-compensated CT image data set for a partially and cyclically moving object will now also be proposed, in particular from a patient with a beating heart, which comprises the following method steps:

detection or transfer of a projection data set from a computed tomography system covering a pre-determined motion phase and a projection angle range, which enables the direct reconstruction of a CT image data set, determination according to the invention of a motion field, reconstruction of a final CT image data set with a second image resolution using a motion-compensating reconstruction method based on a second reconstruction algorithm and the motion field, and storage of the final CT image data set or output of the final CT image data set to an image reproduction system.

In addition to the methods according to embodiments of the invention, the inventors also propose a computer system for image reconstruction, having a memory unit for computer programs and a processor for carrying out the stored computer programs, at least one computer program being stored in the memory unit, the program carrying out the steps of an embodiment of the methods according to an embodiment of the invention during operation of the computer system.

A CT system with a computer system as described above also belongs within the scope of the invention.

BRIEF DESCRIPTION OF THE DRAWINGS

The invention and example embodiments will now be described by reference to the drawings, wherein only the features necessary for an understanding of the invention are described. The following reference signs are used: 1: CT system/C-arm system; 2: first X-ray tube; 3: first detector; 4: second X-ray tube; 5: second detector; 6: gantry housing; 7: pivot arm; 8: patient support; 9: system axis; 10: computer system; 11: contrast medium applicator; 12: ECG-line; P: patient; Prg1-Prgn: computer programs.

In the drawings.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The foundation of at least one embodiment of the present invention is an improved formulation of the motion estimation with the aid of motion-compensated reconstruction algorithms. Therefore, the result of a motion-compensated reconstruction of a "best phase" image $f_{bp}(x,s)$ depends directly on the parameters $s \in \mathbb{R}^{K_{mm}}$, which describe the motion. The parameters s are to be estimated such that the result fulfils particular image properties. Formally seen, this can be achieved by minimizing a cost function $\mathcal{L}(s)$ as an evaluation measure. If an analytical reconstruction algorithm, for example, the FDK algorithm (FDK=Feldkamp-Davis-Kress), is used for reconstruction of the "best-phase" image, an efficient calculation rule can be defined which iteratively determines the parameters for the motion-compensated reconstruction by way of image properties of the reconstructed image, for example, entropy, gradient descent, total variation or the like. Thus, from the CT data of a CT image data set at a single observation time point or a single observation phase of a motion cycle—without the necessity of using CT image data at another observation time point or at another observation phase of the motion cycle—a motion field can be determined, with which a motion-compensated reconstruction can be performed.

Furthermore, in order to reduce the calculation effort, the target function can only be calculated over the portion of the image which contains motion. Formally expressed, therefore, a motion card is calculated which gives the probability that a motion artifact is present at the specific site in the image.

Building thereon, with the method according to at least one embodiment of the invention, the motion taking place in the diagnostically relevant irradiation time—that is, the motion field describing the motion—is to be assessed as precisely as possible.

For this purpose, the following procedure is proposed:
Using the measurement data pin the cost function $$L(\vec{s}) = \|p_{in}(t) - A(\vec{x}, \vec{s}) f(\vec{x}, \vec{s})\|^2. \qquad \text{Equation (1)}$$

can be defined. f denotes the image vector for grey-scale values, A is the voxel-based projector which models the CT-imaging system. The vector $\vec{s}$ ($\vec{x}$,t) denotes the motion field at time t, defined at the vertices $\vec{x}$ of the voxel in the image space. $\vec{s}^{-1}$ denotes the inverse transformation.

The motion field can essentially be calculated in an optimization function, i.e. the following optimization problem must be solved.

$$\min \arg \vec{s}\ L = \|p_{in} - A(\vec{x}, \vec{s}) f(\vec{x}, \vec{s})\|^2. \qquad \text{Equation (2)}$$

Applying a gradient method, the update equation is obtained for the motion field:

$$\vec{s}_{k+1} = \vec{s}_k + \gamma \cdot \frac{\partial L(\vec{s}_k)}{\partial \vec{s}}. \qquad \text{Equation (3)}$$

The step length γ may depend here on the iteration step k.

Derivation of the cost function is determined by the parameters of the motion field as:

$$\frac{\partial L(\vec{s}_k)}{\partial \vec{s}} = 2 \cdot L(\vec{s}_k) \cdot \frac{\partial}{\partial \vec{s}}(A(\vec{x}, \vec{s}) f(\vec{s})) = \qquad \text{Equation (4)}$$

$$2 \cdot L(\vec{s}_k) \cdot \left( \frac{\partial}{\partial \vec{s}} A(\vec{x}, \vec{s}) \cdot f(\vec{s}) + A(\vec{x}, \vec{s}) \cdot \frac{\partial}{\partial \vec{s}} f(\vec{s}) \right)$$

It is problematic that the direction derivative of the projector A cannot easily be determined, since in, for example, a finite difference method, the motion field must be varied in the three spatial directions at each vertex in the image volume, and each configuration must be projected in the data space.

It is therefore proposed according to least one embodiment of the invention to transform the cost function from Equation (1) into the image space by observing the back-projected signals. Thus for the transformed cost function, the following is produced:

$$\hat{L}(\vec{s}) = \|Q(\vec{s})(p_{in} - A(\vec{x}, \vec{s}) f(\vec{x}, \vec{s}))\|^2 \qquad \text{Equation (5)}$$

where $Q(\vec{s})$ denotes the motion-compensating back-projector.

When $f(\vec{x}, \vec{s}) = Q(\vec{s}) \cdot p_{in}$, the following applies:

$$\frac{\partial}{\partial \vec{s}} \hat{L}(\vec{s}) = 2 \cdot L(, \vec{s}) \cdot \frac{\partial}{\partial \vec{s}}(Q(\vec{s})(p_{in} - A(\vec{x}, \vec{s}) Q(\vec{s}) p_{in}) = \qquad \text{Equation (6)}$$

$$2 \cdot L(\vec{s}) \cdot \frac{\partial}{\partial \vec{s}}(Q(\vec{s})(1 - T(\vec{s})) \cdot p_{in})$$

where $T(\vec{s}) = A(\vec{x}, \vec{s}) Q(\vec{s})$;

The operator T, as a composition of back-projection and forward projection, represents a low pass filter, and 1−T therefore represents a high pass filter. The back-projector Q contains the convolution with a convolution kernel typical for computed tomography, and also the back-projection of the filtered signals into the image space. The term $Q(\vec{s})(1-T(\vec{s}))$ therefore only changes the filter characteristics of the back-projection. Ignoring $T(\vec{s})$, the following results:

$$\frac{\partial}{\partial \vec{s}} \hat{L}(\vec{s}) = 2 \cdot \hat{L}(\vec{s}) \cdot \frac{\partial}{\partial \vec{s}} Q(\vec{s}) \cdot p_{in} = 2 \cdot \hat{L}(\vec{s}) \cdot \frac{\partial}{\partial \vec{s}} f(\vec{x}, \vec{s}). \qquad \text{Equation (7)}$$

Calculation of $$\frac{\partial}{\partial \vec{s}} f(\vec{x}, \vec{s})$$

is simple, since the back-projection of the filtered measurement value projection $\hat{p}_{in}$ can be written as $$f(\vec{x}, \vec{s}) = \sum_i \hat{p}_{in}(i, B(i, \vec{x}')) \qquad \text{Equation (8)}$$

Here, $B(i, \vec{x}')$ denotes the back-projection coordinates of the CT geometry in the i-th projection, and the following is obtained:

$$\frac{\partial}{\partial s_{i,y}} f(\vec{x}, \vec{s}) = \frac{\partial}{\partial u'} \hat{p}_{in}(i, u') \cdot \frac{\partial B(i, y')}{\partial y'}. \qquad \text{Equation (9)}$$

With equations (3) and (7), the motion field can be determined in an iterative manner. The motion field can be subject to different mandatory conditions, for example, low-pass filtration. Furthermore, possible boundary conditions can be given for the motion field. A raw data-based approximation of equation (7) is obtained if the raw data-based cost function from equation (2) is used therein.

Based on this underlying concept, the inventors propose the following method and devices:

The fundamental core of least one embodiment of the invention is a method for determining a motion field, comprising a large number of location-specific motion vectors in an image space of a CT image data set for a partially and cyclically moving object, in particular from a patient with a beating heart, comprising the following method steps:

detection or transfer of a projection data set from a computed tomography system covering a pre-determined motion phase and a projection angle range, which enables the direct reconstruction of a CT image data set, iterative determination of the motion field by minimizing a cost function from CT image data sets which are motion-compensated and reconstructed making use of motion fields and which have a first image resolution, with a first analytical reconstruction algorithm, said cost function being transformed into the image space, and storage and/or output of the motion field.

Thus, in the method according to least one embodiment of the invention—in contrast to the prior art—the movement is not determined by comparison of two or more image data sets, but only from the data of a single image data set—comprising a plurality of tomographic 2-D sectional images recorded during the same time interval and distributed across the z-axis of the recording CT system, or a single 3-D image—the motion vectors of a motion field are determined, in that motion vectors are sought which finally lead, by way of a motion-compensating reconstruction—that is, a reconstruction in which the calculation of the tomographic representation takes place using a motion field and for compensation of the location-specific motion described therein—to a reconstructed image of this type, wherein one or more image properties which represent a measure of the motion unsharpness of an image, is optimized so that a minimum motion unsharpness can be assumed. To determine the motion field, the cost function according to Equation 5 is used.

In order to generate an image that is, from the outset, as sharp as possible, it is advantageous if the projection angle range from which the detector data originate is 180° plus the fan-beam angle of a ray beam used for scanning. This corresponds to the minimum of the projection angle range with which, using conventional reconstruction techniques, tomographic images can be created.

It is also proposed that one of the following methods is used for analytical reconstruction: FDK-reconstruction methods (FDK=Feldmann-Davis-Kress), Clack-Defrise-reconstruction methods, reconstruction methods based on Hilbert transformations, reconstruction methods based on Fourier transforms, Radon methods.

As optimization criteria for determining the motion field, for example, one or more of the following image properties can be used: entropy, sum of the gradients, total variation/total fluctuation, compressibility.

It can also be favorable if, for carrying out the method according to the invention—as is usual in the case of cardiographic reconstructions—detector data for generating the projection data sets used are gathered from a plurality of motion cycles. For example, detector data can be gathered from a plurality of heartbeats, in each case, from a possibly relatively narrow pre-determined phase region, until the required projection angle range has been scanned, so that by this means, merely due to the detector data used for the reconstruction, the smallest possible motion unsharpness is produced, which is then further reduced by the method according to least one embodiment of the invention.

It can further be advantageous if the whole region of a tomographic representation is not used for determining a motion field, but rather the motion field is calculated over only a partial region of the object. By this, the necessary computational effort can firstly be reduced and, secondly, can be limited to actually relevant regions, so that artifacts lying outside said regions do not interfere.

On the basis of least one embodiment of the method described above for determining the motion field, a method for generating a motion-compensated CT image data set for a partially and cyclically moving object will now also be proposed, in particular from a patient with a beating heart, which comprises the following method steps:

detection or transfer of a projection data set from a computed tomography system covering a pre-determined motion phase and a projection angle range, which enables the direct reconstruction of a CT image data set, determination according to the invention of a motion field, reconstruction of a final CT image data set with a second image resolution using a motion-compensating reconstruction method based on a second reconstruction algorithm and the motion field, and storage of the final CT image data set or output of the final CT image data set to an image reproduction system.

Thus a motion-compensating reconstruction calculation is carried out on the basis of the motion field determined according to least one embodiment of the invention and a tomographic representation is calculated, wherein the motion artifacts are at least largely remedied. Overall, therefore, proceeding from "best phase" detector data, a further improved tomographic representation is produced without the use of further detector data beyond the detector data already needed to reconstruct the representation.

Although it is essentially possible to base both the calculation of the motion field and the calculation of the final image equally on spatial resolutions, it is however advantageous if the first image resolution—for the calculation of the motion field—is lower than the second image resolution—of the final CT representation.

It can also be favorable if the second reconstruction algorithm differs from the first reconstruction algorithm. By this means, for example, in the context of determining the motion field, a relatively simple analytical algorithm can be used which permits the fastest possible reconstructions and, for the final reconstruction of the CT imaging, a more complex algorithm is used, which generates an optimized image.

It should be noted that, within the context of the determination of the motion field, it is not necessary for only a single reconstruction algorithm to be used. It is also possible, initially to determine the motion field roughly with the aid of a very simple "coarse" reconstruction of the motion field, and subsequently to carry out "fine tuning" of the motion field using a more complex reconstruction method.

Whilst the first reconstruction algorithm must be an analytical algorithm, the second reconstruction algorithm can be an analytical, iterative or non-analytical reconstruction algorithm and the application of per se known subsequent image improvements lies within the scope of the invention.

Furthermore, the detector data for creating the projection data sets used can be collected from one, or a plurality of, motion cycles.

In addition to the methods according to embodiments of the invention, the inventors also propose a computer system for image reconstruction, having a memory unit for computer programs and a processor for carrying out the stored computer programs, at least one computer program being stored in the memory unit, the program carrying out the steps of an embodiment of the methods according to an embodiment of the invention during operation of the computer system.

A CT system with a computer system as described above also belongs within the scope of the invention.

Figure 1:
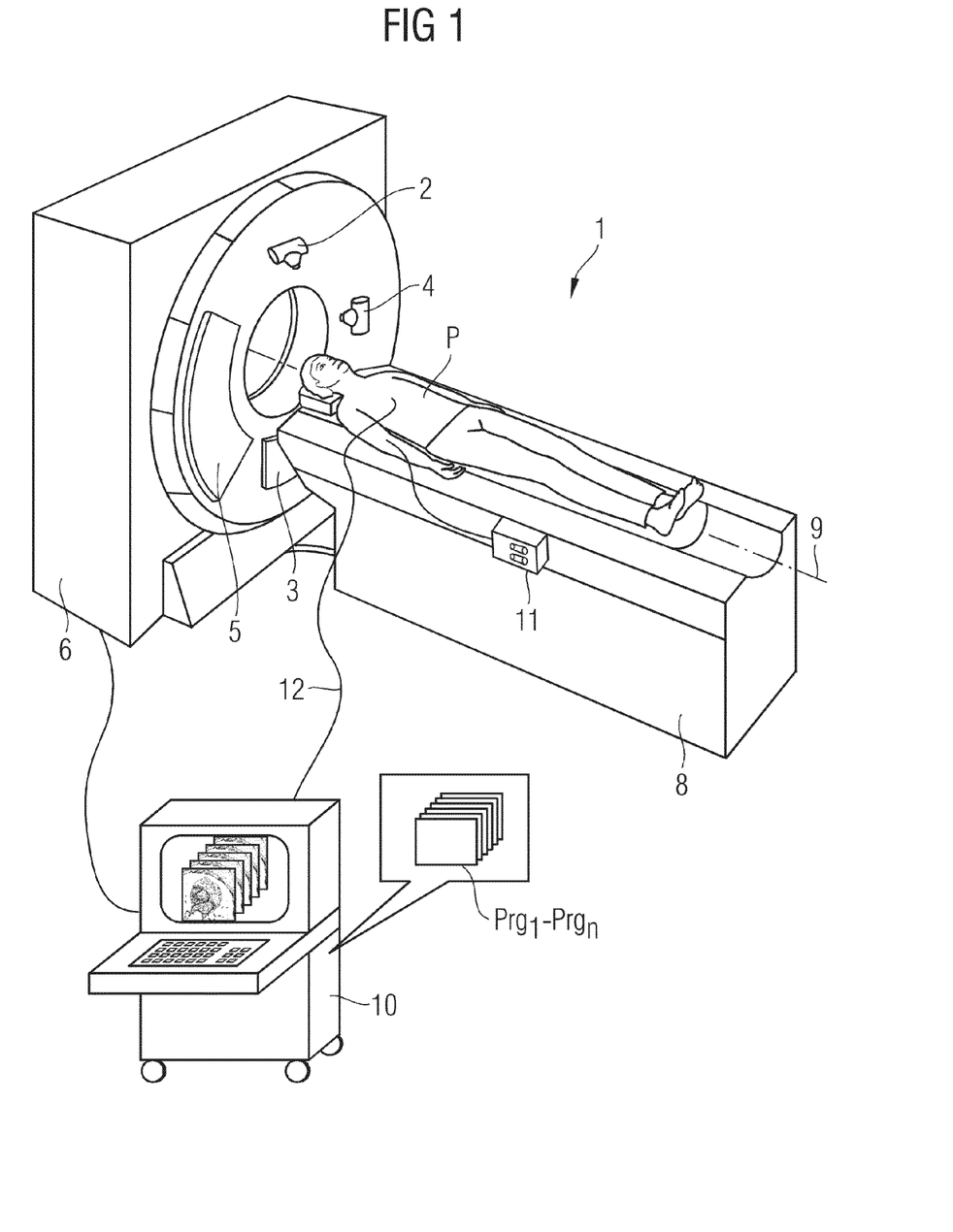
FIG. 1 is a CT system for carrying out the method according to an embodiment of the invention.

FIG. 1 shows, by way of example, a CT system 1 having a computer system 10 with which the method according to the invention can be carried out. The CT system 1 has a first tube/detector system with an X-ray tube 2 and a detector 3 positioned opposite thereto. Optionally, said CT system 1 can have a second X-ray tube 4 with a detector 5 arranged opposite thereto. Both tube/detector systems are arranged on a gantry which is arranged in a gantry housing 6 and rotates about a system axis 9 during scanning. The patient P lies on a displaceable patient support 8, which is displaced, either continuously or sequentially along the z-axis or system axis 9 through the scanning field situated in the gantry housing 6, wherein the attenuation of the X-rays emitted by the X-ray tubes is measured by the detectors.

During the measurement, a contrast medium bolus can be injected into the patient P by means of a contrast medium applicator 11, so that blood vessels are more readily identifiable or a perfusion measurement can be carried out. In the case of cardiographic imaging, with the aid of an ECG line 12, the heart action can also be measured and ECG-gated scanning carried out.

Control of the CT system and performance of an embodiment of the method according to an embodiment of the invention is carried out with the aid of a computer unit, in which computer programs Prg1 to Prgn are held which are able to carry out an embodiment of the method according to an embodiment of the invention as described above. In addition, the output of image data can also be carried out with the computer unit 10.

Figure 2:
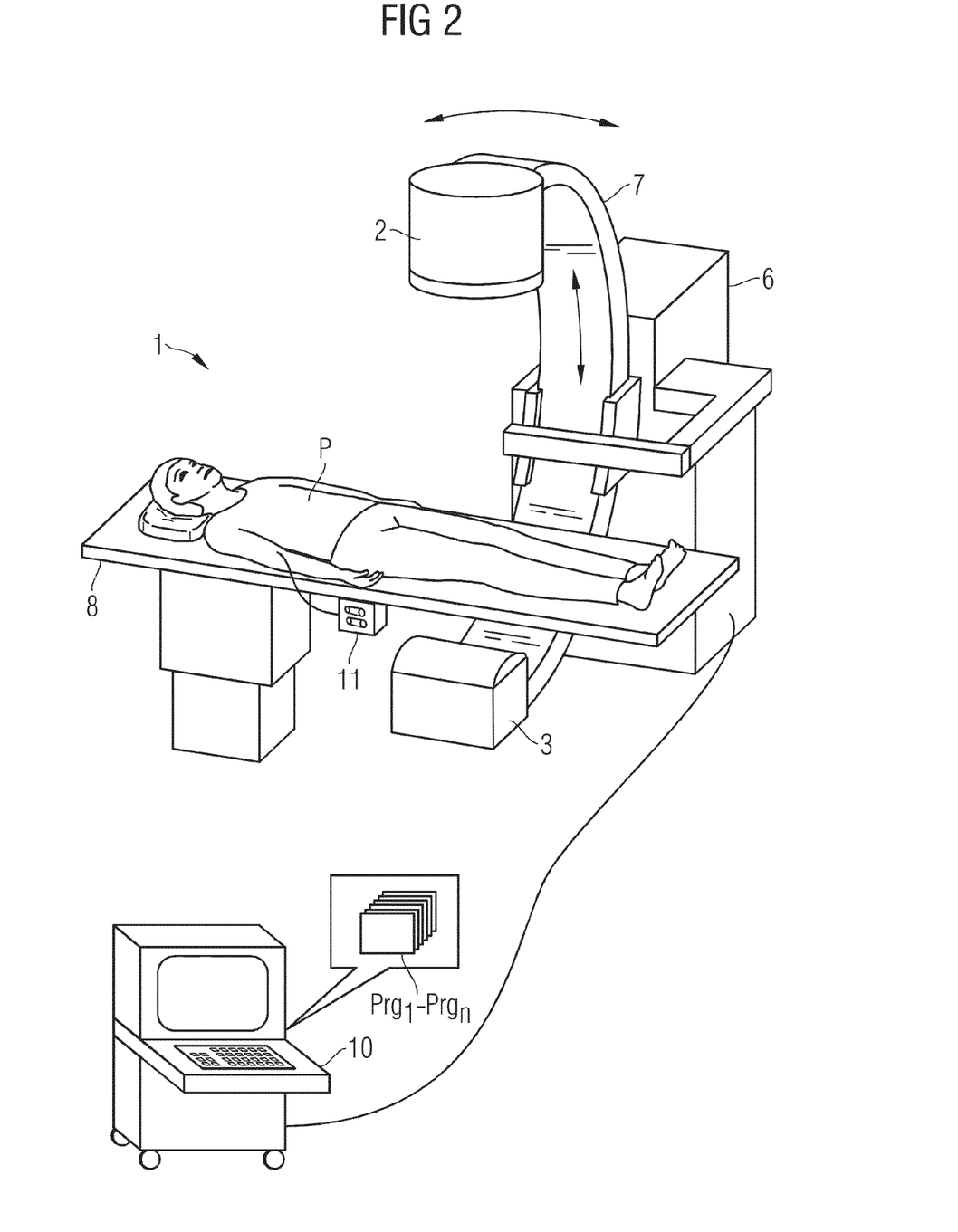
FIG. 2 is a C-arm system for carrying out the method according to an embodiment of the invention.

Alternatively, the method according to an embodiment of the invention can also be carried out in conjunction with the detector data of a CT system in the manner of a C-arm system 1, as shown in FIG. 2. The C-arc system 1 shown here also has an X-ray tube 2 with a detector 3 which is configured planar and is arranged opposing said X-ray tube. Both systems are to be pivoted with the aid of a pivot arm 7 in any position about the patient P. The patient P is situated on a patient support 8 which also has a contrast medium application system 11 in order to inject contrast medium for imaging blood vessels.

Furthermore, with said C-arm system, ECG scanning for determining the heart cycle and the cycle phases embedded therein can be carried out.

The system is also controlled by way of the computer unit 10 which holds computer programs Prg1 to Prgn in the memory thereof, which are able, inter alia, to carry out an embodiment of the method according to an embodiment of the invention for determining a motion field and, with the aid of the motion field, to carry out optimized motion-compensating reconstruction of tomographic image data.

Figure 3:
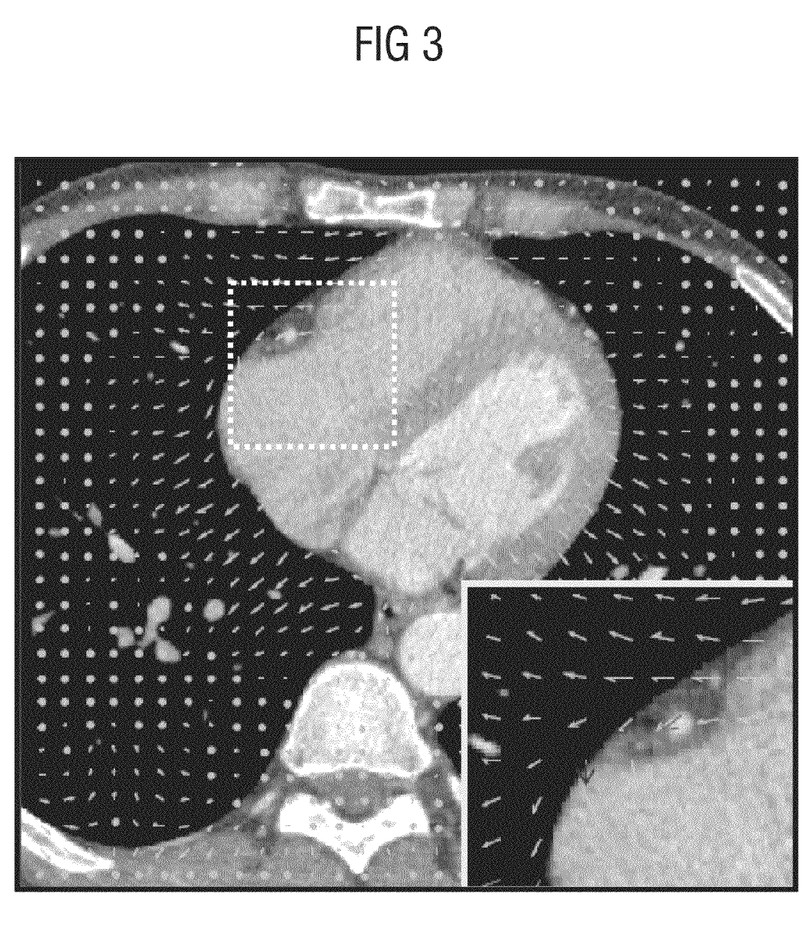
FIG. 3 is a CT sectional image reconstructed without any motion compensation and with overlaid motion field.

FIG. 3 shows a tomographic CT sectional image reconstructed without motion compensation and with a motion field shown overlaid and consisting of a large number of motion or displacement vectors. The vectors or vector bundles, each at a vertex, denote a measure of the probability of displacement of the respective vertex in the direction shown due to the motion unsharpness found in the reconstructed image.

Also shown in the figure is a section outlined with a dotted rectangle, shown enlarged on the right-hand side at the bottom of the figure. In the enlargement, the strength of the individual motion vectors can be particularly well seen, the direction thereof being particularly clearly indicated in the edge region of the heart imaged. The motion field was determined using a cost function transformed into the image space and the derivative thereof $$\frac{\partial}{\partial \vec{s}} \hat{L}(\vec{s}) = 2 \cdot \hat{L}(\vec{s}) \cdot \frac{\partial}{\partial \vec{s}} f(\vec{x}, \vec{s}) \qquad \text{Equation (10)}$$

As described above, the result of a motion-compensated reconstruction of an image $f_{bp}(x,s)$ depends directly on the parameters $s \in \mathbb{R}^{K_{mn}}$, which describe the motion. According to an embodiment of the invention, said parameters s, which correspond to motion vectors, are determined in that image properties of an image reconstructed with motion-compensation using the parameters are optimized. This can take place, for example, by minimizing a cost function $\mathcal{L}(s)$ as an evaluation measure based on a large number of image data sets reconstructed with different motion fields, wherein the motion field is changed until an optimum of the cost function is reached.

Since, for this purpose, an efficient reconstruction rule which iteratively determines the parameters s for the motion-compensating reconstruction via one or more image properties, for example, a gradient descent, is to be provided, an analytical reconstruction algorithm should be used for the motion-compensating reconstruction. Furthermore, in order to reduce the computational effort, the motion field can also only be calculated over the part of an image that is expected to contain relevant motion.

In order to determine the motion field, a motion model can be used. A motion model of this type M: $\mathbb{N} \times \mathbb{R}^3 \times \mathbb{R}^K \mapsto \mathbb{R}^3$ calculates the actual location x'=M(i,x,s) at the original location x at the time of recording the i-th projection, based on the parameters s. An example of a motion model is a dense motion field. For every location y in the J-th projection image, there exists a displacement vector $s_{j,y} \in \mathbb{R}^3$. Formally expressed, this means:

$$M(i,x,s) = x + s_{i,x} = x'. \qquad \text{Equation (11)}$$

In the context of an embodiment of the invention, however, the application of other, thinly occupied motion fields, for example, consisting of B-splines or other linear base functions and non-linear base functions, e.g. NURBS (=Non-uniform rational B-splines), is possible.

As a concrete example for a motion-compensating reconstruction algorithm, reference is made to the per se known motion-compensating FDK-reconstruction algorithm, which is disclosed in the document by Schafer et al. cited above. This FDK-algorithm is one of the most commonly used algorithms in clinical CT. Mathematically, said algorithm can be described with the following back-projection formulae f: $\mathbb{R}^3 \times \mathbb{R}^K \mapsto \mathbb{R}$:

$$f(x, s) \sim \sum_i Q(i, x') p(i, A(i, x')) \qquad \text{Equation (12)}$$

$$f(x, s) \sim \sum_i Q(i, x') p(i, u') \qquad \text{Equation (13)}$$

The function p: $\mathbb{N} \times \mathbb{R}^2 \mapsto \mathbb{R}$ enables access to the convoluted projection values p(i,u) of the i-th projection image at the detector location u. The function A: $\mathbb{N} \times \mathbb{R}^3 \mapsto \mathbb{R}^2$ forms a 3-D image location x at the 2-D detector location u=A(i,x) in the i-th projection image. The exact formula is dependent on the system geometry used. The function Q: $\mathbb{N} \times \mathbb{R}^3 \mapsto \mathbb{R}$ is a weighting function for correcting data redundancies. The exact formulation depends on the system geometry and the recording mode.

A decisive component of the present approach is the definition of a suitable cost function. In the literature, it has been shown that, for example, the compactness or compressibility of the image is suitable measure for detecting image artifacts. Examples thereof are the entropy, general measures of compressibility, for example, based on the cosine or wavelet transformation, or the TV (total variation) norm.

Entropy is given here as an actual example embodiment, so that the cost function is calculated as follows:

$$\mathcal{L}(s) = -\sum_h P(h, s) \ln P(h, s), \qquad \text{Equation (14)}$$

where P:HU×$\mathbb{R}^k \mapsto [0,1]$ gives the probability of the occurrence of an image value in Hounsfield units, that is, a CT value h∈HU in the reconstructed image f(x,s). The calculation of the target value can be carried out over the whole image or only in a partial region of the image Ω, which is determined over a motion map (see below). Determination of the probability function can be carried out, for example, analytically via a Parzen window density estimation, which is defined as follows:

$$P(h, s) = \frac{1}{|\Omega|} \sum_{x \in \Omega} K(f(x, s) - h). \qquad \text{Equation (15)}$$

The Parzen window density estimation is based on a kernel function K, for example, a Gaussian kernel, for which the following applies:

$$K(x) = \frac{1}{\sqrt{2\pi}} \exp\left(-\frac{1}{2\sigma^2} x^2\right). \qquad \text{Equation (16)}$$

The standard deviation σ>0 determines the smoothness of the density function P.

With the aid of a motion map, the determination of the motion field according to an embodiment of the invention can be restricted to only a relevant partial region of the image which actually shows motion artifacts. In concrete terms, this is carried out by limiting the calculation to a partial quantity of all the possible image locations of the overall image. Adaptation of said image locations is directly reflected in the calculation formulae. By using a motion map of this type, the calculation time can be reduced, the sensitivity of the image size can be increased, and therefore an improved image quality can be achieved. The motion map here defines a partial quantity Ω of the image volume to be reconstructed.

Two examples for the determination of a motion map follow:

calculation of two adjacent phase-correlated reconstructions. The quantity Ω is all pixels for which the absolute difference exceeds a threshold value.

calculation of two adjacent phase-correlated reconstructions. A 3-D/3-D registration is carried out. The set Ω is all pixels for which the motion vector exceeds a threshold value.

According to an embodiment of the invention, the motion estimation, that is, the estimation of a motion field, is performed from a large number of location-specific motion or displacement vectors by means of an optimization algorithm. Herein, the parameters which minimize the cost function $\mathcal{L}$ are sought. The following therefore applies:

$$\hat{s} = \arg\min_{s \in \mathbb{R}^{K_{mm}}} \mathcal{L}(s). \qquad \text{Equation (17)}$$

Any image criteria or image properties can be used for defining an optimization problem of this type, for example, the entropy of the reconstructed image, the total variation or compressibility of the image data, wherein the minimization or maximization of one or more image properties reveals an optimally determined motion field. For rapid and stable calculation, the analytical derivation of all the components presented—that is, the reconstruction and evaluation function—can be calculated. The optimization problem formulated in this way is solved by using an optimization method, such as methods of steepest descent, Newtonian methods, stochastic optimization methods, evolutionary optimization methods or by an exhaustive search.

In order to favor particular solutions, the optimization problem can also be enhanced in the context of the invention with a regularization term $\mathcal{R}(s)$. This makes it possible to favor particular properties of the motion field. An example here is the total of the lengths of the motion vectors. Each motion leads to a raised regularization value, whereas the image evaluation level becomes smaller. Depending on the weighting of the two terms, a solution is sought which optimizes the image size and the regularization term to the best possible extent. Mathematically, the parameters can thus be described using an additive term, as follows:

$$\hat{s} = \arg\min_{s \in \mathbb{R}^{K_{mm}}} \mathcal{L}(s) + \mathcal{R}(s). \qquad \text{Equation (18)}$$

The proposed method thus enables, for the first time, the improvement of a "best-phase" reconstruction by motion estimation and compensation of the motion. Furthermore, the proposed method can be used to improve other motion or heart phases or for noise reduction or for better dosage utilization. The motion map enables high sensitivity and rapid calculation of the method disclosed, since all the components can be rapidly calculated, making possible use in the clinical setting.

Figure 4:
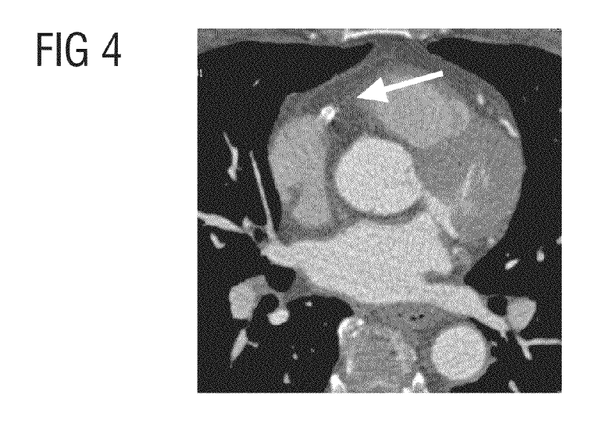
FIG. 4 is a tomographic CT sectional image of a heart from a dual source CT examination.
Figure 5:
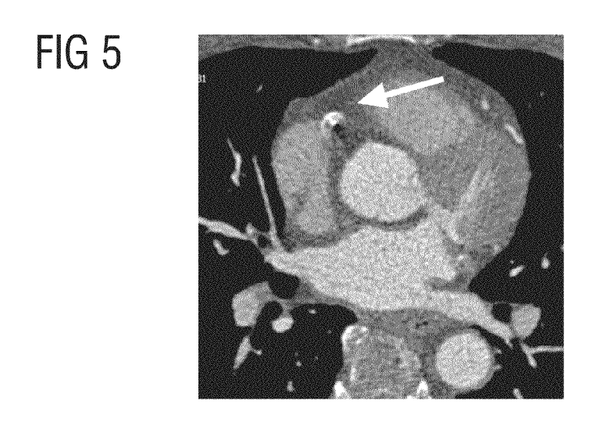
FIG. 5 is a tomographic CT sectional image of a heart from a single source CT examination.
Figure 6:
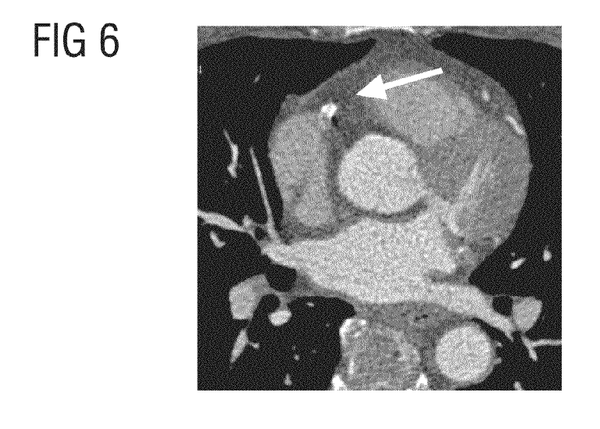
FIG. 6 is a tomographic CT sectional image of a heart from a single source CT examination, reconstructed using the motion-compensating reconstruction according to an embodiment of the invention.

Shown in FIGS. 4 to 6 with a CT sectional image from a cardiological examination is the reduction of the movement unsharpness in a "best-phase" image. In FIG. 4, a "best-phase" sectional image of the heart from a conventional reconstruction based on a dual source CT scan is shown. FIG. 5 shows the same section, but reconstructed using data from a scan with a single source CT. FIG. 6 shows the same section again, also reconstructed using data from a scan with a single-source CT, but using the method according to the invention. All the detector data originate from a heart phase of 74% of the cycle. As can be seen, the motion unsharpness for the dual source recording (FIG. 4) is very low, whereas the temporal resolution in the conventionally reconstructed single-source recording (FIG. 5) is not sufficient to reproduce the coronary artery (indicated by the arrow) artifact-free. However, by the use of the method according to the invention with the same data set, as used in FIG. 5, the motion artifacts can be significantly reduced, so that from the single-source data, an almost artifact-free representation as per FIG. 6 results.

Summarizing, therefore, it is proposed with an embodiment of the invention that, by use of the projection data from a single CT image data set, to determine a motion field by finding extreme values of at least one image property in motion-compensating reconstructed tomographic image data sets iteratively and using a cost function transformed into the image space of the CT image data set and, furthermore, using the motion field thus determined and the aforementioned projection data, to create a final CT representation by way of motion-compensating reconstruction.

More precisely expressed, a method is proposed for determining a motion field in an image space of a CT image data set for a partially and cyclically moving object, wherein a projection data set of a CT system is recorded for a predetermined motion phase and a projection angle range, and an iterative determination of the motion field is carried out by minimizing a cost function from CT image data sets which are motion-compensated and reconstructed making use of motion fields and which have a first image resolution, with a first analytical reconstruction algorithm, said cost function being based on raw data or being transformed into the image space. Furthermore, a method for generating a motion-compensated CT image data set of a partially and cyclically moving object is proposed wherein, through reconstruction, a final CT image data set having a second image resolution is generated using a motion-compensating reconstruction method based on a second reconstruction algorithm and a motion field which has been determined according to the method described above.

Although the invention has been illustrated and described in detail using the example embodiments, the invention is not restricted by the examples disclosed, and other variations can be derived herefrom by a person skilled in the art without departing from the protective scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a motion field, including a plurality of location-specific motion vectors in an image space of a CT image data set for a partially and cyclically moving object, the method comprising:
   detecting or transferring a projection data set from a computed tomography system covering a motion phase and a projection angle range, to enable direct reconstruction of a CT image data set;
   iteratively determining the motion field by minimizing a cost function from CT image data sets which are motion-compensated and reconstructed making use of motion fields and which have a first image resolution, with a first analytical reconstruction algorithm, the cost function being based on raw data or transformed into the image space; and
   at least one of storing and outputting the motion field;
   wherein, as the raw data-based cost function, the equation min arg$\vec{s}$ L=$\|p_{in} - A(\vec{x}, \vec{s}) f(\vec{x}, \vec{s})\|^2$ is used.

2. The method of claim 1, wherein the projection angle range is 180° plus the fan-beam angle of a ray beam used.

3. The method of claim 2, wherein the analytical reconstruction method is a method from the following list:
   FDK-reconstruction methods (FDK=Feldmann-Davis-Kress),
   Clack-Defrise-reconstruction methods,
   reconstruction methods based on Hilbert transformations,
   reconstruction methods based on Fourier transforms, or
   Radon methods.

4. The method of claim 1, wherein the analytical reconstruction method is a method from the following list:
   FDK-reconstruction methods (FDK=Feldmann-Davis-Kress),
   Clack-Defrise-reconstruction methods,
   reconstruction methods based on Hilbert transformations,
   reconstruction methods based on Fourier transforms, or
   Radon methods.

5. The method of claim 4, wherein, as the image property to be optimized, at least one of the following image properties is used:
   entropy,
   $L^2$-norm of the difference between the reconstructed raw data and the "synthetic" data determined with motion-sensitive forward projection,
   total variation/total fluctuation, and
   compressibility.

6. The method of claim 1, wherein, as the image property to be optimized, at least one of the following image properties is used:
   entropy,
   $L^2$-norm of the difference between the reconstructed raw data and the "synthetic" data determined with motion-sensitive forward projection,
   total variation/total fluctuation, and
   compressibility.

7. The method of claim 1, wherein the detector data for generating the used projection data sets are collected from a plurality of motion cycles.

8. The method of claim 1, wherein the motion field is calculated over only a partial region of the object.

9. The method of claim 1, wherein the detector data for creating the projection data sets used is collectable from one or a plurality of motion cycles.

10. The method of claim 1, wherein the detector data for creating the projection data sets used is collectable from one or a plurality of motion cycles.

11. A non-transitory computer readable medium including program segments for, when executed on a computer device, causing the computer device to implement the method of claim 1.

12. A method for generating a motion-compensated CT image data set for a partially and cyclically moving object, the method comprising:
    detecting or transferring a projection data set from a computed tomography system covering a motion phase and a projection angle range, to enable the direct reconstruction of a CT image data set;
    determining a motion field according to the method of claim 1;
    reconstructing a final CT image data set which has a second image resolution using a motion-compensated reconstruction method based on a second reconstruction algorithm and the motion field; and
    at least one of storing the final CT image data set and outputting the final CT image data set to an image reproduction system.

13. The method of claim 12, wherein the first image resolution is relatively lower than the second image resolution.

14. The method of claim 13, wherein the second reconstruction algorithm differs from the first reconstruction algorithm.

15. The method of claim 12, wherein the second reconstruction algorithm differs from the first reconstruction algorithm.

16. The method of claim 15, wherein the second reconstruction algorithm is an analytical reconstruction algorithm.

17. The method of claim 15, wherein the second reconstruction algorithm is an iterative reconstruction algorithm.

18. The method of claim 15, wherein the second reconstruction algorithm is a non-analytical reconstruction algorithm.

19. A non-transitory computer readable medium including program segments for, when executed on a computer device, causing the computer device to implement the method of claim 12.

20. A computer system, comprising:
    a memory unit, configured to store computer programs; and
    a processor configured to carry out the stored computer programs, at least one of the computer programs being stored in the memory unit, the at least one computer program carrying out, operation of the computer system, at least the following:
    detecting or transferring a projection data set from a computed tomography system covering a motion phase and a projection angle range, to enable direct reconstruction of a CT image data set;
    iteratively determining a motion field by minimizing a cost function from CT image data sets which are motion-compensated and reconstructed making use of motion fields and which have a first image resolution, with a first analytical reconstruction algorithm, the cost function being based on raw data or transformed into the image space; and
    at least one of storing and outputting the motion field,
    wherein, as the raw data-based cost function, the equation $\min \arg \vec{s}\ L = \|p_{in} - A(\vec{x}, \vec{s})f(\vec{x}, \vec{s})\|^2$ is used.

21. A CT system comprising the computer system of claim 20.

22. A computer system for image reconstruction, comprising:
    a memory unit, configured to store computer programs; and
    a processor configured to carry out the stored computer programs, at least one of the computer programs being stored in the memory unit, the at least one computer program carrying out, operation of the computer system, at least the following:
    detecting or transferring a projection data set from a computed tomography system covering a motion phase and a projection angle range, to enable the direct reconstruction of a CT image data set;
    determining a motion field by at least,
        detecting or transferring a projection data set from a computed tomography system covering a motion phase and a projection angle range, to enable direct reconstruction of a CT image data set,
        iteratively determining a motion field by minimizing a cost function from CT image data sets which are motion-compensated and reconstructed making use of motion fields and which have a first image resolution, with a first analytical reconstruction algorithm, the cost function being based on raw data or transformed into the image space, and
        at least one of storing and outputting the motion field;
    reconstructing a final CT image data set which has a second image resolution using a motion-compensated reconstruction method based on a second reconstruction algorithm and the motion field; and
    at least one of storing the final CT image data set and outputting the final CT image data set to an image reproduction system,
    wherein, as the raw data-based cost function, the equation $\min \arg \vec{s}\ L = \|p_{in} - A(\vec{x}, \vec{s})f(\vec{x}, \vec{s})\|^2$ is used.

23. A CT system comprising the computer system of claim 22.

* * * * *